(12) United States Patent
Luque Vera et al.

(10) Patent No.: US 12,114,652 B2
(45) Date of Patent: Oct. 15, 2024

(54) DEVICE FOR EVAPORATING VOLATILE SUBSTANCES

(71) Applicant: ZOBELE ESPAÑA, S.A., Barcelona (ES)

(72) Inventors: Sergio Luque Vera, Barcelona (ES); Ruben Garcia Fabregas, Barcelona (ES); John Hainsworth, Barcelona (ES)

(73) Assignee: ZOBELE ESPAÑA, S.A. (ES)

(*) Notice: Subject to any disclaimer, the term of this patent is extended or adjusted under 35 U.S.C. 154(b) by 0 days.

(21) Appl. No.: 15/537,526

(22) PCT Filed: Dec. 10, 2015

(86) PCT No.: PCT/ES2015/070893
§ 371 (c)(1),
(2) Date: Jun. 19, 2017

(87) PCT Pub. No.: WO2016/097439
PCT Pub. Date: Jun. 23, 2016

(65) Prior Publication Data
US 2017/0347640 A1    Dec. 7, 2017

(30) Foreign Application Priority Data
Dec. 19, 2014 (ES) ............................... ES201431891

(51) Int. Cl.
*A01M 1/20*      (2006.01)
*A61L 9/03*      (2006.01)

(52) U.S. Cl.
CPC ............ *A01M 1/2077* (2013.01); *A01M 1/20* (2013.01); *A61L 9/03* (2013.01); *A61L 9/037* (2013.01)

(58) Field of Classification Search
CPC ....... A01M 1/2077; A01M 1/20; A61L 9/037; A61L 9/03
See application file for complete search history.

(56) References Cited

U.S. PATENT DOCUMENTS 2,586,380 A * 2/1952 Quercia ................... F23Q 2/44
431/323
5,722,201 A * 3/1998 Diorio ................... A01G 27/06
47/79

(Continued)

FOREIGN PATENT DOCUMENTS

EP       1 509 081       3/2005
ES       2 300 589 T3    6/2008

(Continued)

OTHER PUBLICATIONS

International Search Report mailed Mar. 8, 2016 in corresponding PCT International Application No. PCT/ES2015/070893.

(Continued)

*Primary Examiner* — Regina M Yoo
(74) *Attorney, Agent, or Firm* — OSTROLENK FABER LLP

(57) ABSTRACT

A device for evaporation of volatile substances, comprising a housing; a container removably mounted in the housing containing liquid volatile substances; a wick of a porous material, provided with a first end and a second end, wherein at least the first end is contained inside the container; a resistor element arranged to contact the second end of the wick; and connecting means for connecting the device to the mains supply to allow the heating of the resistor element; wherein the resistor element is a coiled wire that forms a compressing spring, and wherein the resistor element is compressed and in contact with the second end of the wick when the container is mounted in the housing.

7 Claims, 1 Drawing Sheet

(56) References Cited

U.S. PATENT DOCUMENTS

| | | | | |
|---|---|---|---|---|
| 6,790,408 B2* | 9/2004 | Whitby | A01M 1/2077 | 261/100 |
| 6,859,615 B2* | 2/2005 | Yip | A61L 9/037 | 392/390 |
| 6,909,840 B2* | 6/2005 | Harwig | A01M 1/2072 | 392/395 |
| 7,036,800 B2* | 5/2006 | Ellis | A01M 1/205 | 261/26 |
| 7,530,313 B2* | 5/2009 | Chamlee | F42C 1/04 | 102/254 |
| 2001/0005573 A1* | 6/2001 | Furner | F21V 37/00 | 431/292 |
| 2001/0012495 A1* | 8/2001 | Furner | A01M 29/12 | 422/126 |
| 2003/0071030 A1* | 4/2003 | Zobele | A01M 1/2077 | 219/390 |
| 2004/0003724 A1* | 1/2004 | Ellis | A01M 1/205 | 96/115 |
| 2005/0175331 A1* | 8/2005 | Tam | A01M 1/2072 | 392/405 |
| 2006/0115386 A1* | 6/2006 | Michaels | A01M 1/205 | 422/123 |
| 2006/0193611 A1* | 8/2006 | Ruiz Ballesteros | A61L 9/037 | 392/394 |
| 2006/0243820 A1* | 11/2006 | Ng | B05B 17/0646 | 239/102.1 |
| 2007/0159422 A1* | 7/2007 | Blandino | A01M 1/2033 | 345/82 |
| 2007/0218413 A1* | 9/2007 | Heng-Wei | F23D 3/26 | 431/320 |
| 2010/0059601 A1* | 3/2010 | Bankers | A01M 1/2077 | 239/44 |
| 2013/0192623 A1* | 8/2013 | Tucker | H01C 17/00 | 131/329 |
| 2013/0298905 A1* | 11/2013 | Levin | A24F 47/008 | 128/202.21 |
| 2014/0205272 A1* | 7/2014 | Midgette | A01M 1/2077 | 392/395 |
| 2015/0320116 A1* | 11/2015 | Bleloch | A61M 15/06 | 219/628 |
| 2016/0150828 A1* | 6/2016 | Goldstein | A24F 47/008 | 392/387 |
| 2016/0151528 A1* | 6/2016 | Duffield | A01M 1/2044 | 261/128 |
| 2017/0181472 A1* | 6/2017 | Batista | A24F 47/008 | |

FOREIGN PATENT DOCUMENTS

| | | | | | |
|---|---|---|---|---|---|
| GB | 1514338 | * | 6/1978 | | F23D 3/16 |
| GB | 2175994 A | * | 12/1986 | | F21S 13/00 |
| JP | 03007522 A | * | 1/1991 | | A01M 1/20 |
| JP | H03-7522 A | | 1/1991 | | |
| WO | WO-03103387 A2 | * | 12/2003 | | A01M 1/2072 |
| WO | WO 2004/002542 A1 | | 1/2004 | | |
| WO | WO 2006/052519 A2 | | 5/2006 | | |
| WO | WO 2006/124757 A2 | | 11/2006 | | |

OTHER PUBLICATIONS

Written Opinion mailed Mar. 8, 2016 in corresponding PCT International Application No. PCT/ES2015/070893.

* cited by examiner

DEVICE FOR EVAPORATING VOLATILE SUBSTANCES

CROSS-REFERENCE TO RELATED APPLICATIONS

The present application is a 35 U.S.C. §§ 371 national phase conversion of PCT/ES2015/070893, filed Dec. 10, 2015, which claims priority to Spanish Patent Application No. P201431891, filed Dec. 19, 2014, the contents of which are incorporated herein by reference. The PCT International Application was published in the Spanish language.

OBJECT OF THE INVENTION

The present invention relates to a device for evaporation of volatile substances for the odorisation or deodorisation of air and for disinfecting, and more specifically, for the evaporation of fragrances or insecticides.

An object of the invention is to provide a device for evaporation of volatile substances able to provide a more rapid response to changes in the input power, to allow, on the one hand, achieving a higher concentration of the substance in the environment when the device is connected to the mains, and on the other hand, to allow the perception of changes in the concentration of substances in the environment by the user.

It is also an object of the invention to provide a more efficient device for evaporation of volatile substances, which is capable of reducing the consumption of electrical energy.

Finally, it is an object of the invention to provide a simple device, easy to manufacture and to assemble, that reduces the number of parts used, to reduce accordingly the cost associated with the product.

BACKGROUND OF THE INVENTION

Traditionally, the devices for evaporation of volatile substances of the air fresheners and insecticides type comprise a heating element and a replaceable refill element.

Typically, the heating element uses a thermistor with positive temperature coefficient (PTC) powered by the mains to generate heat, and thus increase the temperature of the materials of the device. The refill element comprises a container containing a liquid formulation, fragrance or insecticide, and a capillary wick intended for extracting the liquid formulation from the container and delivering it outside the device.

In use, the refill element is mounted in the housing of the device, so that the wick is near the area of the device that is heated by the thermistor. The heat generated by said thermistor is transferred to the wick by convection from the heated surfaces of the device. This heat causes evaporation of the volatile formulation from the wick.

This heat transfer to the volatile fluid is considerably inefficient, since in order to transfer heat to the wick it is necessary to significantly increase both the temperature of the solid materials close to the wick and the air surrounding it. In this way, it is necessary that the device reaches a temperature higher than that required in the wick to perform the evaporation selected by the user.

Document EP1509081 describes an evaporator device that uses batteries to feed at least one heating element to contact the wick of the refill element. While the described device improves the heat transfer to the volatile fluid, the device requires a specific assembly to ensure contact of the wick with the refill element. This specific assembly involves a complexity and an added cost to the device.

According to the above, in view of the state of the art, there is therefore a need for a device for evaporation of volatile substances that improve the performance of heat transfer to the volatile fluid, reduce the consumption of electrical energy, and at the same time, is simple and inexpensive, of easy manufacture and assembly.

DESCRIPTION OF THE INVENTION

The device for evaporation of volatile substances that the present invention proposes is presented as an improvement over that which is known from the state of the art, since it successfully achieves the objectives set forth above as suitable for the art.

The invention is a device for evaporation of volatile substances which comprises a housing, a container removably mounted in the housing and containing volatile liquid substances, a wick of a porous material, provided with a first end and a second end, where, at least the first end of the wick is contained inside the container, a resistor element arranged to contact the second end of the wick, and means for connecting the device to the mains supply to allow the heating of the resistor element. In addition, and according to the present invention, the resistor element is a coiled wire that forms a compressing spring, wherein the resistor element is compressed and in contact with the second end of the wick when the container is mounted in the housing.

By providing a compressing spring as a resistor element, the device allows to ensure contact of the wick with the resistor element, thanks to the intrinsic elasticity of the spring. In addition, by arranging this spring so it is compressed at one end of the wick when the container is mounted in the housing, the device allows adjusting the pressure exerted on the wick.

Also by arranging the resistor element in contact with the second end of the wick, the invention improves the heat transfer from the resistor element to the liquid volatile substances contained in the container, and consequently improves the performance of the device of the invention with respect to the conventional devices for evaporation of volatile substances.

This improved heat transfer increases the evaporation rate and generates a more rapid response, with respect to conventional devices, to changes in the input power.

Likewise, obtaining a more rapid response to changes in the input power allows, on the one hand, reducing the existing normal delay between connection or power on of the device and the obtaining of a significant or effective fragrance or insecticide concentration in the environment, and secondly, and especially in the case of fragrance dispensing, it offers the possibility of using power on and off cycles to generate remarkable variations in the intensity of the fragrance.

In this way, the device of the invention causes greater satisfaction to the user, allowing that he/she perceives, more quickly and to a greater extent, the smell delivered by the device. This satisfaction is due to the fact that, traditionally, extended delays in the perception of the device operation after it being plugged in or powered on, caused confusion to the user about the operative status of the device and having to verify, sometimes, if it really was running. In the case of insecticide dispensers, the device of the invention provides better protection to the user.

In addition, since the device allows using power on and off cycles and is able to quickly adjust the variation in the fragrance delivery rate, the device allows generating evaporations of different intensity, counteracting the tendency of users to become used to the fragrance. The promptness of the change of intensity and the intensity itself of these evaporation help improve the user satisfaction.

Likewise, by performing an improved heat transfer, based on direct contact of the resistor element with one end of the wick, the device performs a more efficient use of energy, therefore causing the decrease of the electrical energy consumed by the device.

On the other hand, by forming the resistor element as a compressing spring, the device does without any additional assembly conventionally required to ensure contact between the resistor element and the wick. In this way, the invention provides a simplified device, with fewer parts, and easy to manufacture and assemble.

In addition, by providing means for connecting the device to the mains, the device allows to increase the concentration of substances evaporated in the environment for a long time. These connecting means improve user satisfaction, since in the case of using batteries, the prolonged use of a high substance delivery rate would make batteries quickly be exhausted.

According to a preferred embodiment, the resistor element has such elasticity that when the container is mounted in the housing, it exerts a predetermined pressure on the second end of the wick that ensures the maintenance of at least one point of contact with said second end. Thus, by varying the elasticity of the spring, the device ensures the contact of the resistor element with the second end of the wick, without damaging said wick, while allowing a certain tolerance in the contact with it. This tolerance allows establishing contact between the resistor element and the second end of the wick, regardless of the possible variations in height of the containers. In this way, contact problems caused by the so variable geometries of containers are reduced.

According to another preferred mode for carrying out the invention, the second end of the wick has a surface of evaporation, wherein the surface of evaporation has at least one point of contact with the resistor element.

Preferably, the second end of the wick is in contact with at least half the length of the resistor element when compressed.

Preferably, the resistor element has a helical configuration. By varying the resistor configuration, and specifically the helical configuration thereof, the device allows to vary the number of points (or surface) of contact between the resistor element and the second end of the wick, thus providing more or less contact between both elements.

Preferably, the resistor element comprises nickel-chromium. Alternatively, and equally preferably, the resistor element comprises a nickel, chromium, and aluminium alloy.

Preferably, the liquid volatile substances are fragrances. Alternatively, the liquid volatile substances are insecticides.

DESCRIPTION OF THE DRAWINGS

To complete the description that is going to be made and to assist a better understanding of the invention's characteristics, according to a preferred practical mode for carrying out the invention, accompanying as an integral part of said description is a set of drawings, where in an illustrative and non-limiting way, the following is represented:

FIG. 1.

FIG. 2.

PREFERRED MODE FOR CARRYING OUT THE INVENTION

Figure 1A:
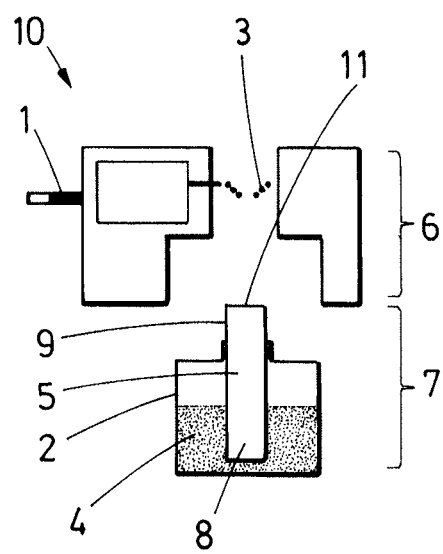
—FIGS. 1a and 1b show a schematic view of a cross-section of the device for evaporation of volatile substances when the container is removed (FIG. 1a) and mounted (FIG. 1b) in the housing of the device, according to a preferred mode for carrying out the present invention.
Figure 1B:
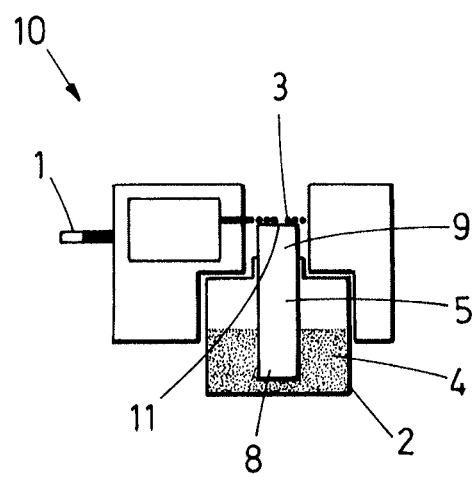

As FIGS. 1a and 1b show, the device 10 for evaporation of volatile substances consists of two main components, a housing 6 and a replaceable refill element 7.

The replaceable refill element 7 consists of a container 2 susceptible of being removably mounted in the housing 6 and containing liquid volatile substances 4, and a wick 5 of a porous material, provided with a first end 8 and a second end 9, both ends being opposite, and wherein, at least the first end 8 of the wick 5 is contained inside the container 2.

The housing 6 houses a resistor element 3, arranged to contact the second end 9 of the wick 5, and means 1 for connecting the device 10 to the mains 1 to allow the heating of the resistor element 3.

According to the present invention, the resistor element 3 is a coiled wire which forms a compressing spring, wherein as shown in FIG. 1b, said resistor element 3 is compressed and in contact with the second end 9 of the wick 5 when the container 2 is mounted in the housing 6.

As can be seen in FIGS. 1a and 1b, the resistor element 3 is a spring whose ends are contained in separated planes, in such a manner that when the container 2 is mounted in the housing 6, the resistor element 3 is compressed and in contact with the second end 9 of the wick 5.

Preferably, this contact between the resistor element 3 and the second end 9 of the wick 5 is produced through a surface of evaporation 11 provided in the second end 9 of the wick 5.

The resistor element 3 contacts directly the second end 9 of the wick 5. In this way, the device 10 improves the heat transfer from the resistor element 3 to the liquid volatile substances 4 contained in the container 2, increasing the rate of evaporation of the volatile substances 4, and generating a quicker response to changes in the input power.

Figure 2A:
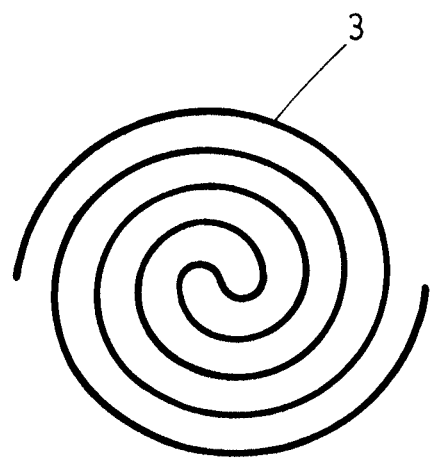
—FIGS. 2a and 2b show, respectively, a plan and side view of the resistor element, according to a preferred mode for carrying out the invention.
Figure 2B:
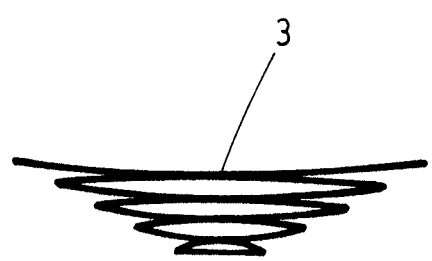

FIGS. 2a and 2b show a plan and side view of the resistor element 3 according to the present invention. According to a preferred mode of carrying out the invention, the resistor element 3 has a trunk-conical helical configuration, wherein the radius of the coil decreases progressively in the direction towards the contact with the second end 9 of the wick 5.

By configuring the resistor element 3 as a spring-type element, the device 10 allows providing a variable contact surface between the resistor element 3 and the second end 9 of the wick 5, changing the configuration of the spring, for example, by varying the configuration of the spring spirals (spiral diameter, separation between them, etc.) in the case that the resistor element 3 has a helical configuration, or by changing the thickness of the resistor element 3 itself.

Likewise, by making the resistor element 3 as a spring, the invention allows doing without additional elements to ensure the contact of the wick 5 with the resistor element 3. In this way, it is achieved that the device 10 of the invention is simpler, requires fewer parts, and involves a lower cost.

Finally, in view of this description and figures, the person skilled in the art will understand that the invention has been described according to preferred embodiments thereof, but that multiple variations can be introduced in said preferred embodiments without departing from the object of the invention as has been claimed.

The invention claimed is:

1. A device for evaporation of volatile substances, comprising:
   a housing,
   a container removably mounted in the housing and containing liquid volatile substances,
   a wick of a porous material, provided with a first end and a second end, wherein at least the first end of the wick is contained inside the container,
   a resistor element arranged to contact the wick,
   a connector connecting the device to a mains supply to allow heating of the resistor element,
   wherein the resistor element is a coiled wire which forms a compressing spring, and wherein the resistor element is arranged to contact the second end of the wick, wherein the resistor element has a trunk-conical helical configuration, wherein the radius of the coiled wire decreases progressively in the direction toward the contact with the second end of the wick, and wherein said resistor element is compressed and in contact with the second end of the wick when the container is mounted in the housing, such that the second end of the wick is in contact with at least half of the length of wire defined by the coiled wire of the resistor element when compressed, whereupon contact between the resistor element and the second end of the wick is ensured due to intrinsic elasticity of the coiled wire, wherein the resistor element has a first spiral portion, a second spiral portion, a central portion connected to the first spiral portion and the second spiral portion, a first end, and a second end, and wherein radius of the first spiral portion of the resistor element decreases progressively from the first end toward the central portion, and radius of the second spiral portion of the resistor element increases progressively in a direction away from the central portion and toward the second end of the resistor element.

2. The device for evaporation of volatile substances, according to claim 1, wherein the second end of the wick has a surface of evaporation, and wherein the surface of evaporation has at least one point of contact with the resistor element.

3. The device for evaporation of volatile substances, according to claim 1, wherein the resistor element comprises nickel-chromium.

4. The device for evaporation of volatile substances, according to claim 1, wherein the resistor element comprises a nickel, chromium and aluminium alloy.

5. The device for evaporation of volatile substances, according to claim 1, wherein the liquid volatile substances are fragrances.

6. The device for evaporation of volatile substances, according to claim 1, wherein the liquid volatile substances are insecticides.

7. The device for evaporation of volatile substances, according to claim 1, wherein the central portion is formed with two bends, and wherein the radius of the first spiral portion of the resistor element decreases progressively from the first end towards the two bends, and the radius of the second spiral portion of the resistor element increases progressively in a direction away from the two bends and toward the second end of the resistor element.

* * * * *